United States Patent [19]

Kutner et al.

[11] Patent Number: 5,248,478
[45] Date of Patent: Sep. 28, 1993

[54] PROCESS AND APPARATUS FOR HEAT DISINFECTING SOFT CONTACT LENSES

[75] Inventors: Barry S. Kutner, Wilton; Daniel A. Latowicki, Newtown, both of Conn.; Kenneth E. Malech, Briarcliff Manor, N.Y.

[73] Assignee: Flexiclave, Inc., Orangeburg, N.Y.

[21] Appl. No.: 835,309

[22] Filed: Feb. 14, 1992

Related U.S. Application Data

[63] Continuation-in-part of Ser. No. 692,736, Apr. 29, 1991, which is a continuation-in-part of Ser. No. 184,246, Apr. 21, 1988, Pat. No. 5,019,344.

[51] Int. Cl.$^5$ ............................................. A61L 2/00
[52] U.S. Cl. ..................................... 422/21; 422/28; 422/294; 422/298; 206/5.1
[58] Field of Search .................... 99/DIG. 14; 422/21, 422/28, 294, 298, 299, 305; 426/107; 219/10.55 M, 10.55 F, 10.55 E; 134/901; 206/5.1

[56] References Cited

U.S. PATENT DOCUMENTS

| | | | |
|---|---|---|---|
| 3,215,539 | 11/1965 | Landy | 99/221 |
| 3,219,460 | 11/1965 | Brown | 99/192 |
| 3,494,722 | 2/1970 | Gray | 21/54 |
| 3,494,724 | 2/1970 | Gray | 21/54 |
| 3,615,713 | 10/1971 | Stevenson | 99/171 |
| 3,676,058 | 11/1972 | Gray | 21/54 |
| 3,753,651 | 10/1973 | Boucher | 219/10.55 |
| 3,924,013 | 12/1975 | Kane | 219/10.55 M |
| 3,998,590 | 12/1976 | Glorieux | 422/307 |
| 4,400,357 | 11/1983 | Hohmann | 422/297 |
| 4,529,868 | 7/1985 | Bowen et al. | 402/307 |
| 4,582,076 | 4/1986 | Prat | 134/53 R |
| 4,591,820 | 9/1987 | Martinez | 206/5.1 |
| 4,808,782 | 2/1989 | Nakagawa et al. | 219/10.55 |
| 4,836,859 | 6/1989 | Konishi et al. | 422/28 |
| 4,848,931 | 7/1989 | Kamada et al. | 219/10.55 E |
| 4,852,591 | 8/1989 | Wisotzki et al. | 134/57 R |
| 4,880,601 | 11/1989 | Anderman et al. | 422/28 |
| 4,971,773 | 11/1990 | Rohrer et al. | 422/21 |

FOREIGN PATENT DOCUMENTS

| | | |
|---|---|---|
| 2584503 | 1/1987 | France . |
| 3-149053 | 6/1991 | Japan . |
| 86/07264 | 12/1986 | World Int. Prop. O. . |

Primary Examiner—Robert J. Warden
Assistant Examiner—Hien Tran
Attorney, Agent, or Firm—Steinberg & Raskin

[57] ABSTRACT

A process for disinfecting soft contact lenses includes introducing disinfecting solution into a vessel that is at least partially formed of material transparent to microwave electromagnetic radiation, and placing the contact lenses into contact with the disinfecting solution within an interior portion of the vessel which is substantially shielded from microwave electromagnetic radiation. The vessel is closed and then subjected to microwave radiation to heat the disinfecting solution with which the lenses are in contact while the lenses themselves are shielded from the radiation. The radiation continues until the lenses are disinfected. Apparatus in accordance with the invention include the vessel, disinfecting solution and in accordance with one embodiment, lens holder apparatus comprising shielding material defining compartments that are receivable of the contact lenses which are in fluid communication with the surrounding interior of the vessel but which provide microwave radiation shielding.

20 Claims, 7 Drawing Sheets

PROCESS AND APPARATUS FOR HEAT DISINFECTING SOFT CONTACT LENSES

This is a continuation-in-part of application Ser. No. 07/692,736 filed Apr. 29, 1991, which is a continuation-in-part of application Ser. No. 07/184,246, filed Apr. 21, 1988, now U.S. Pat. No. 5,019,344.

BACKGROUND OF THE INVENTION

This invention relates generally to processes and apparatus for disinfecting soft contact lenses and, more particularly, to processes and apparatus for disinfecting soft contact lenses by heat disinfection.

In caring for hydrophilic gel (soft) contact lenses, attention must be directed toward, among other things, maintaining lens hydration and protecting the lenses from pathogens. Exposure of soft contact lenses to heat or to the action of soaking solutions are the techniques used to provide the disinfection necessary to protect soft contact lenses from pathogens.

Disinfecting lenses by soaking in germicidal solutions is a two step process which includes soaking the lenses in the solution until the lens is disinfected, and then rinsing the lenses with a rinsing solution prior to insertion. Typically, lenses are stored in a germicidal solution, such as one that derives its germicidal activity from thimerosal or chlorhexidine, for at least four hours and then are rinsed in a saline solution. Such techniques are time consuming, require the user to keep different solutions on hand, and risk eye irritation should the disinfecting solution not be adequately rinsed from the lenses.

For heat disinfection, it is generally necessary to heat soft contact lenses to a temperature of 80° C. for at least 10 minutes. To insure lens hydration, the gel lenses are immersed in saline solution in their storage case which is then placed within a boiling unit. Although gel lenses can be disinfected in a shorter time by heat than by soaking, conventional heat disinfection techniques require a separate heating unit which adds to the expense of lens care. Moreover, in practice, heat disinfection of lenses is a relatively time-consuming procedure which necessitates that the wearer uses an alternate pair of lenses, or eyeglasses, while disinfection proceeds.

SUMMARY OF THE INVENTION

It is an object of the present invention to provide new and improved processes and apparatus for disinfecting soft contact lenses.

Another object of the present invention is to provide new and improved processes and apparatus for disinfecting soft contact lenses by heat.

Still another object of the present invention is to provide new and improved processes and apparatus for the heat disinfection of soft contact lenses in a rapid manner.

A further object of the present invention is to provide new and improved processes and apparatus for disinfecting soft contact lenses by heat using a heating source commonly found in many households thereby eliminating the need to purchase a separate heating unit.

Briefly, in accordance with the present invention, these and other objects are attained by a process in which a disinfecting solution is introduced into a vessel that is at least partially formed of material transparent to microwave electromagnetic radiation, and introducing the soft contact lenses into an interior portion of the vessel that is substantially shielded from microwave electromagnetic radiation, either before or after the disinfecting solution has been introduced, such that the contact lenses are placed into contact with the disinfecting solution. The vessel is closed and then subjected to microwave electromagnetic radiation to heat the disinfecting solution with which the lenses are in contact, while the lenses themselves are shielded from the radiation. Irradiation continues until the lenses are disinfected.

The vessel preferably comprises a collapsible pouch formed of flexible, vapor-impermeable sheet material which expands to a visibly apparent distended condition during the irradiating step to provide a visual indication that disinfection is proceeding.

The irradiating step is preferably accomplished by placing the closed vessel containing the radiation-shielded lenses and disinfecting solution within the cavity of a conventional microwave oven of the type found in many households.

According to one embodiment of the invention, the shielded interior portion of the vessel is provided by lens holder apparatus which comprise shielding means that define compartments that are receivable of the contact lenses. The lens-receiving compartments are in fluid communication with the surrounding interior of the vessel to permit the lenses to be in contact with the disinfecting solution while irradiation continues. In another embodiment of the invention, shielding means are integrated with the vessel, such as by providing shielding material on portions of the vessel wall, to define a shielded interior portion of the vessel.

DESCRIPTION OF THE DRAWINGS

A more complete appreciation of the present invention and many of the attendant advantages thereof will be readily understood by reference to the following detailed description when considered in connection with the accompanying drawings in which:

FIGS. 3a-3d are views of the lens holder apparatus of FIG. 2 for providing a radiation-shielded interior portion of the pouch of FIG. 2 wherein FIG. 3a is a top plan view of the holder apparatus when open, FIG. 3b is a bottom plan view thereof, FIG. 3c is a top plan view of the holder apparatus when closed, and FIG. 3d is a section view taken along line d—d of FIG. 3c;

DESCRIPTION OF THE PREFERRED EMBODIMENTS

Figure 1:
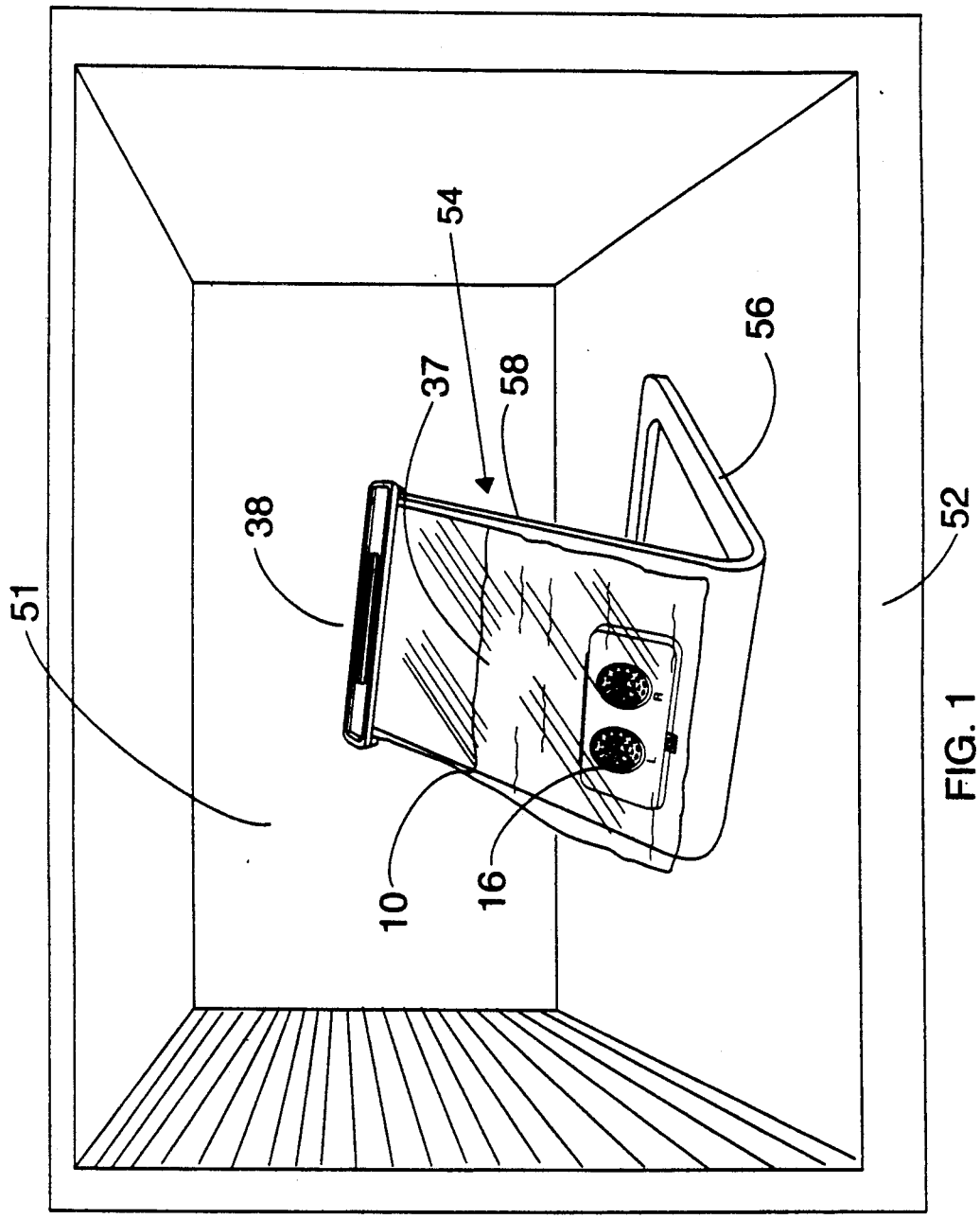
FIG. 1 is an orthogonal view of apparatus for disinfecting soft contact lenses in accordance with one embodiment of the invention.
Figure 2:
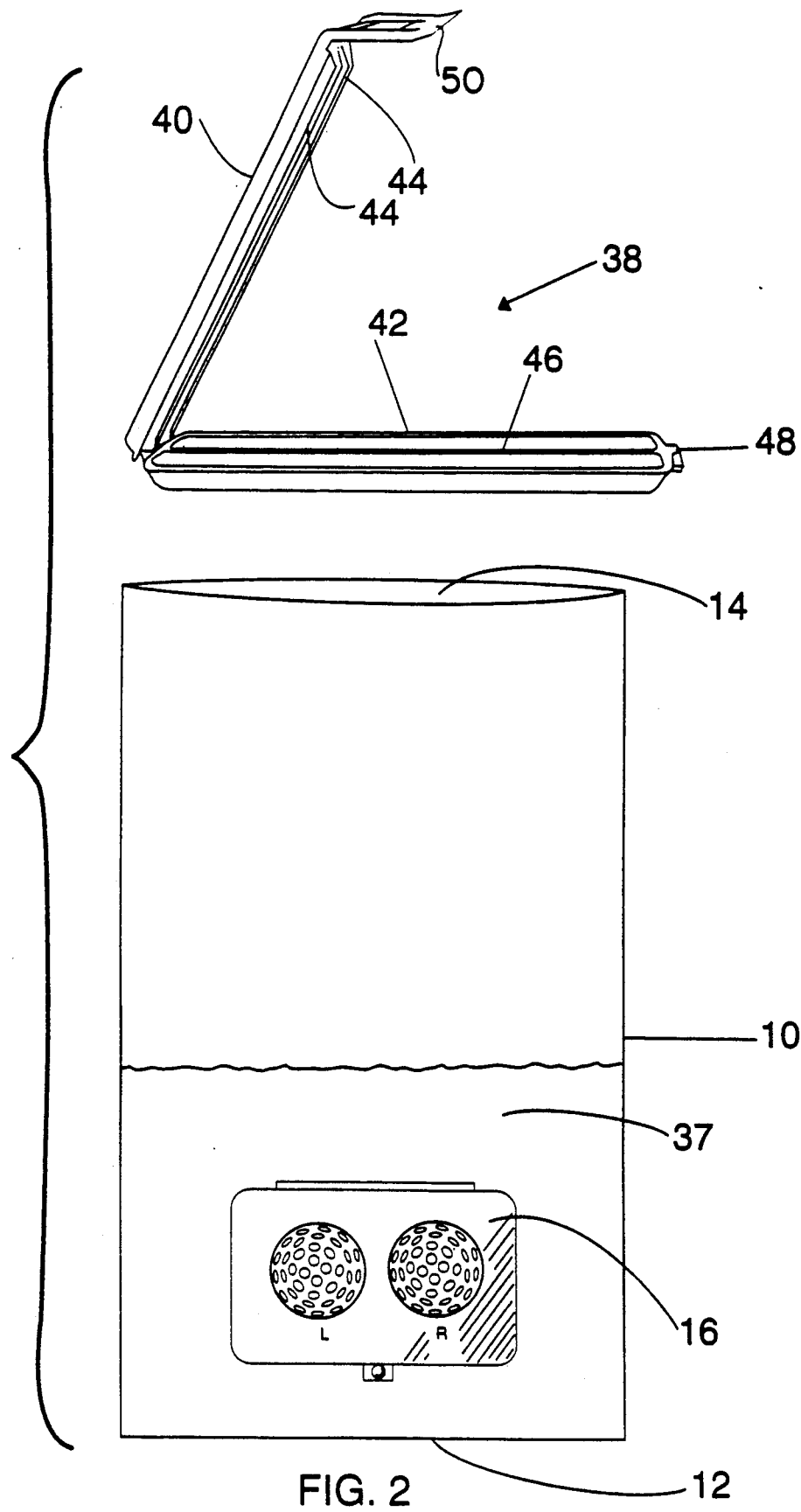
FIG. 2 is an elevation view of an assembly of a pouch, lens holder apparatus and disinfecting solution, including a clamp for sealing the pouch, in accordance with the embodiment of the invention shown in FIG. 1.

Referring now to the drawings wherein like reference characters designate identical or corresponding parts throughout the several views, and more particularly to FIGS. 1-3, apparatus for disinfecting soft contact lenses in accordance with one embodiment of the invention comprises an assembly including a pouch 10 formed of material transparent to microwave electromagnetic radiation which contains a disinfecting solution 37, contact lens-receiving holder apparatus 16 which provides an interior portion of the pouch which is in fluid communication with the remainder of the pouch interior, but which is shielded from microwave radiation, and a clamp 38 for closing the pouch. The closed pouch assembly is supported on a fixture 54 within the cavity 51 of a conventional microwave oven 52 of the type commonly found in many households, as described below.

The pouch 10 (FIG. 2) is formed of flexible sheet material comprising a laminate of polypropylene and polyester transparent to microwave electromagnetic radiation. The pouch 10 may be constructed from a tubular web of such sheet material having a sealed end 12 and an open end or mouth 14.

Figure 3A:
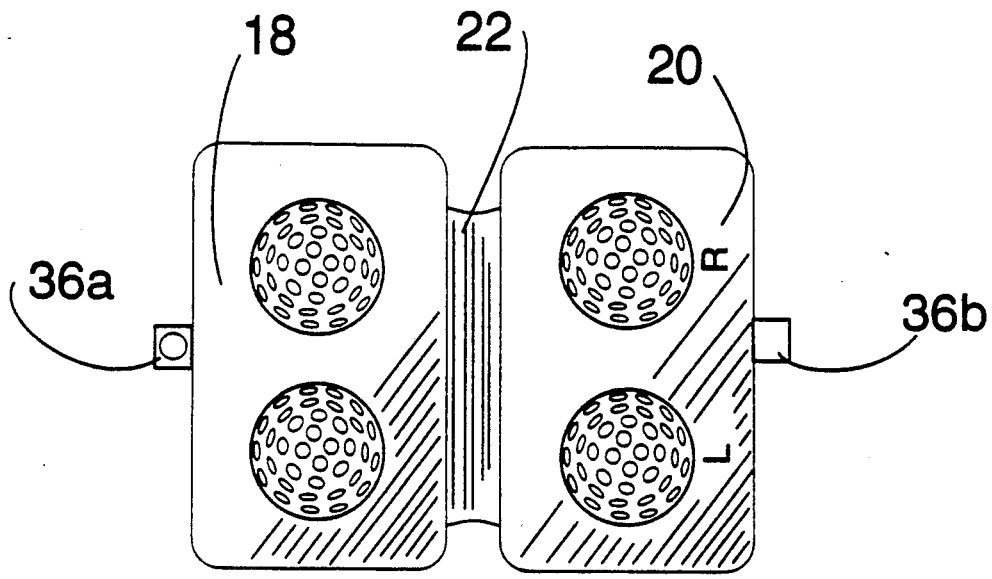
Figure 3B:
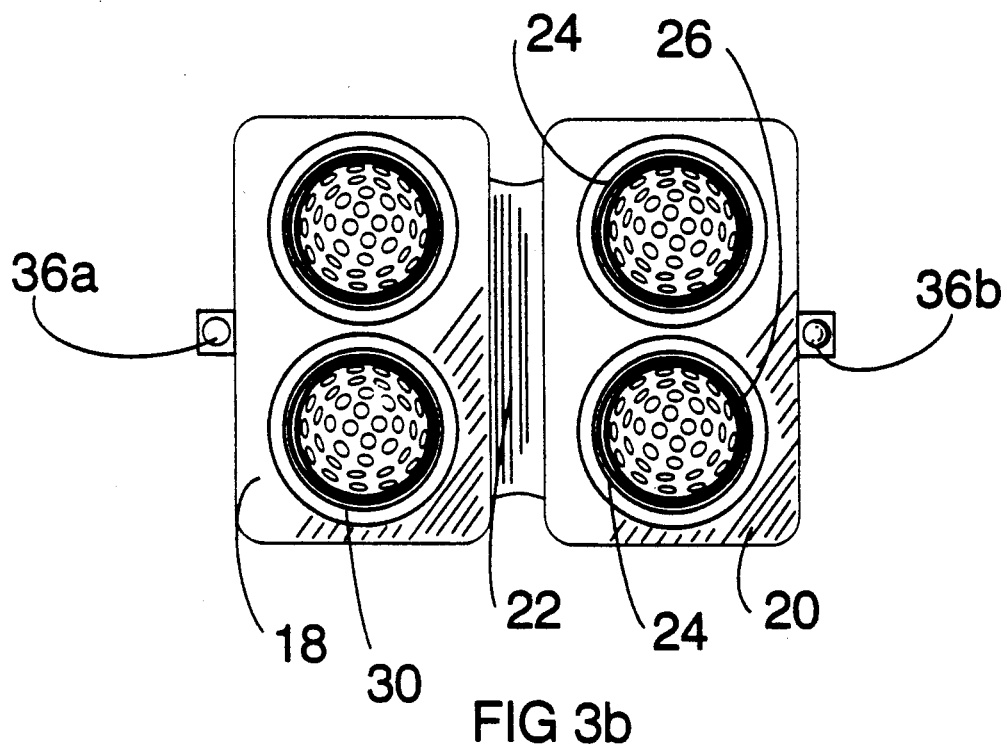
Figure 3C:
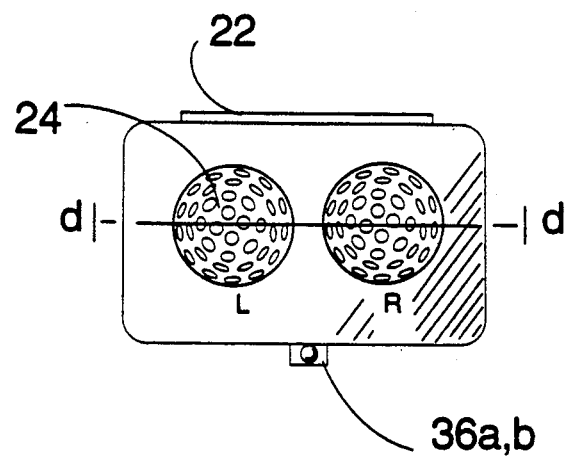
Figure 3D:
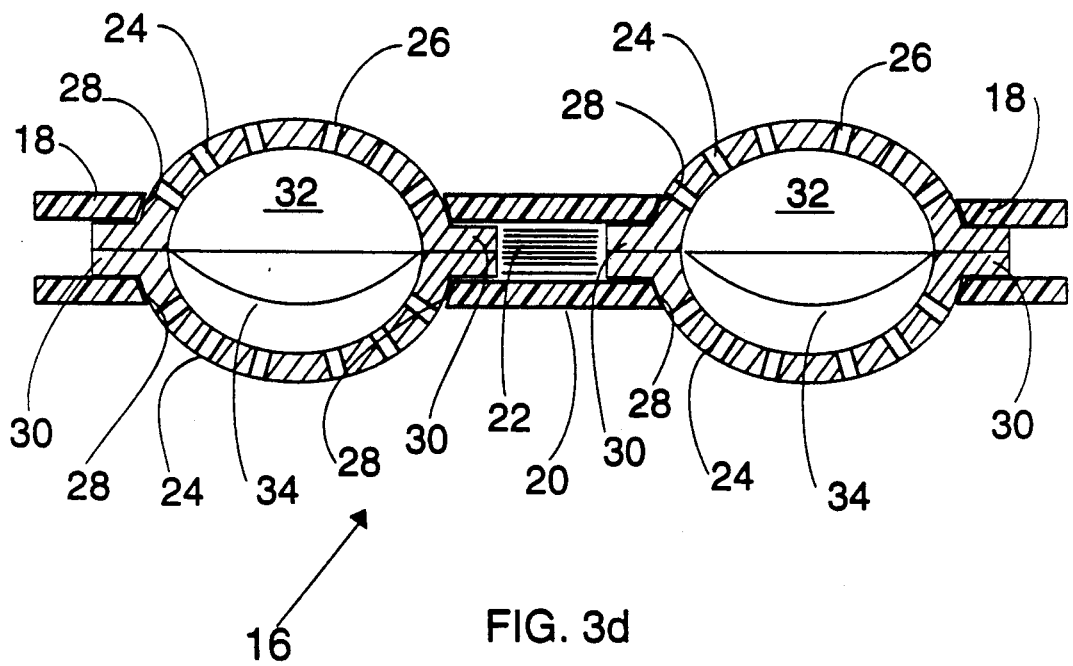

Referring to FIGS. 3a-3d, the lens holder apparatus 16 comprises a pair of planar cover members 18, 20 formed of polypropylene connected to each other by an integral hinge portion 22. A pair of circular openings 28 (FIG. 3d) are formed in corresponding locations in each of the cover members 18, 20 in which substantially dome-shaped members 24 are affixed formed of stainless steel sheet material through which small apertures or perforations 26 are formed. The dome-shaped members are preferably coated with Teflon material to promote removal of the contact lenses from the holder apparatus during use. Each dome-shaped member 24 has a peripheral rim 30 which engages and is affixed to the peripheral region of a respective opening 28 on the inside surface of a respective cover member 18, 20 so that the dome-shaped portion of member 24 extends through the opening 28 and protrudes beyond the outer surface of the cover member. As seen in FIGS. 3c and 3d, upon folding the cover members 18 and 20 onto each other, about hinge portion 22, each dome-shaped member 24 affixed to cover member 18 moves into contiguous relationship with a corresponding dome-shaped member 24 affixed to the other cover member 20, with the peripheral rims 30 of the pairs of contiguous dome-shaped members 24 of cover members 18 and 20 abutting against each other to thereby define a pair of compartments 32 for receiving a pair of contact lenses 34. The interior of the compartments 32 are shielded from exposure to microwave radiation by the metallic material of the dome-shaped members. The apertures 26 formed in the sheet material of the dome-shaped members provide fluid communication between the interiors of compartments 32 and the remainder of the pouch interior. However, the apertures 26 are sufficiently small that microwave electromagnetic radiation is prevented from passing into the interior of the compartments 32. An opening in a locking member 36a connected to cover member 18 is adapted to receive a projection on a locking member 36b connected to cover member 20 when the holder apparatus is closed to secure the holder apparatus in its closed position.

Figure 4A:
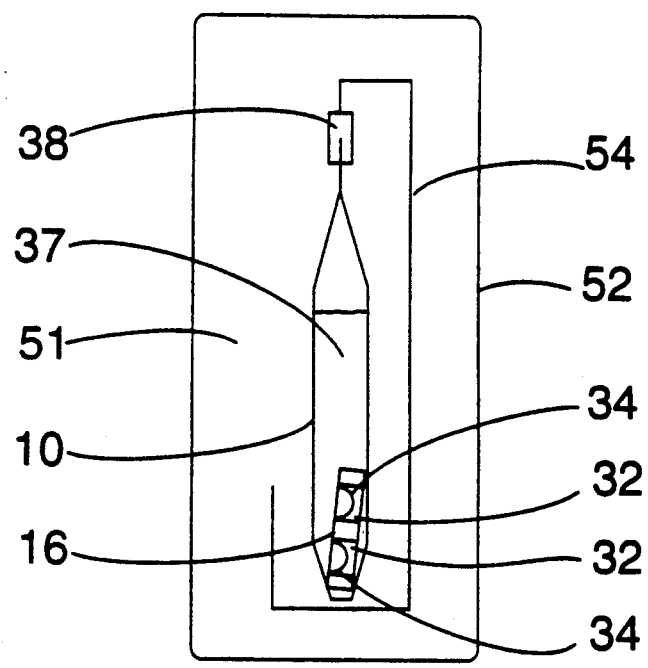
FIGS. 4a and 4b are schematic illustrations depicting a process in accordance with the invention.
Figure 4B:
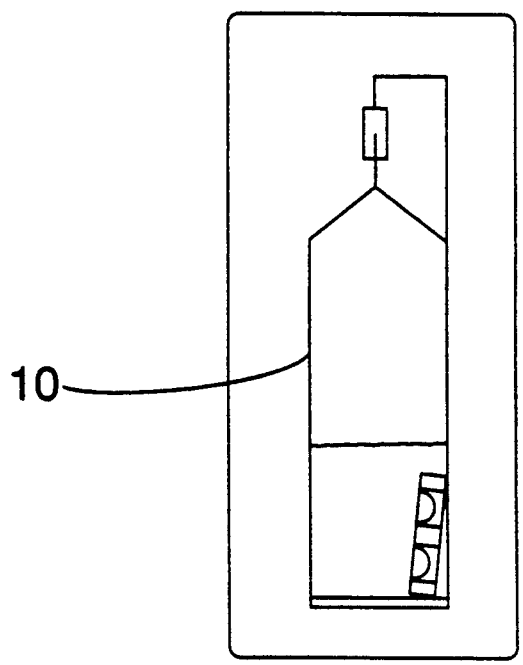

Referring to FIGS. 1 and 4, in the operation of the apparatus in accordance with the process of the invention, the contact lenses 34 are situated in the shielded compartments 32 of the holder apparatus 16 by placing each of them into the concave depression of a respective one of the pair of dome-shaped members 24 of one of the cover members 18, 20, and then closing the holder apparatus as described above whereupon the lenses become situated in respective shielded compartments 32. The clips 36 are applied to lock the holder apparatus.

The holder apparatus 16 containing the contact lenses 34 is introduced into the pouch 10 through its open end or mouth 14. Saline solution 37 is introduced into the pouch so that the holder apparatus 16 is completely immersed in the solution. For example, the saline solution may be introduced using an aerosol dispenser or from a unit dose ampule. Since the apertures 26 provide fluid communication between the interior of the contact lens-receiving compartments 32 and the surrounding pouch interior, the saline solution fills the compartments 32 and contacts the lenses 34. The mouth 14 of pouch 10 is then sealed by means of clamp 38 (FIG. 2) so that the pouch is substantially liquid-tight, but such that vapor generated during the disinfecting process will be vented from the pouch when a threshold internal pressure is exceeded. The clamp 38 is formed of plastic and includes a pair of legs 40, 42 pivotally connected to each other at one of their ends. A pair of longitudinal ribs 44 are formed on leg 40 while a single rib 46 is formed on the other leg 42, positioned to snugly interfit between ribs 44 when legs 40, 42 are closed. When the legs 40, 42 are thus clamped over the mouth 14 of pouch 10, the plastic sheet material of the pouch is tightly corrugated by the ribs 44, 46 to form a liquid-tight seal. A locking protrusion 48 and cooperating latch 50 are provided on the free ends of legs 40 and 42 to lock the clamp 38 to the mouth 14 of pouch 10.

The thus-formed sealed assembly comprising the pouch 10, the saline solution 37 and contact lens-containing holder apparatus 16, is then mounted on the fixture 54 (FIG. 1) and situated in the cavity 51 of the microwave oven 52. Fixture 54 comprises a base 56 from which a planar supporting wall 58 extends upwardly at an angle to the horizontal. The sealed assembly is supported on wall 58 by fastening clamp 38 to its top by any suitable means, such as by Velcro fasteners.

Irradiation of the assembly with microwave electromagnetic radiation then proceeds whereupon the saline disinfectant solution is substantially immediately heated under the thermal effects of the microwave radiation while the contact lenses 34 are shielded from the radiation within compartments 32 of holder apparatus 16. The heated disinfectant solution is in constant contact with the lenses and the lenses are disinfected by heat within a relatively short time.

The embodiment of the invention described above is particularly advantageous insofar as a visual indication that disinfection is proceeding. In particular, as the sealed assembly is irradiated, the disinfectant solution 37 begins to vaporize. As the vapor pressure within pouch 10 increases, the pouch 10 expands to a distended condition, schematically depicted in FIG. 4b, to provide an easily recognizable visual indication that disinfection is proceeding. Vapor is vented from within the pouch when the internal pressure exceeds a certain threshold to eliminate any possibility of rupture of the pouch.

In one specific embodiment of the invention, the pouch 10 has a volume of about 50 cc, and is filled with about 20 cc of saline solution. The sealed assembly is irradiated with microwave electromagnetic radiation at a power of about 700 watts for about 30 seconds. Under these conditions, the temperature of the saline solution is increased to 100° C. in several seconds, and disinfection of the contact lenses is completed in about 30 seconds. In accordance with the invention, the volume of disinfectant solution is generally in a range of between about 10 to 40 cc, while the assembly is irradiated with radiation at a power in the range of between about 500 to 1000 watts for a time in the range of between about 15 to 60 seconds. The pouch clamp 38, fixture 54 and cover members of the lens holder apparatus are preferably formed of polypropylene and the dome-shaped members 24 of the holder apparatus 16 are preferably formed of stainless steel.

Another advantage of the invention described above is that irradiation of the sealed assembly may continue until the disinfecting solution 37 itself is substantially disinfected. The pouch 10 is maintained in a sealed condition after completion of the irradiating step with the lenses in contact with the disinfectant solution. In this manner, the lenses are protected from recontamination until future use.

Figure 5:
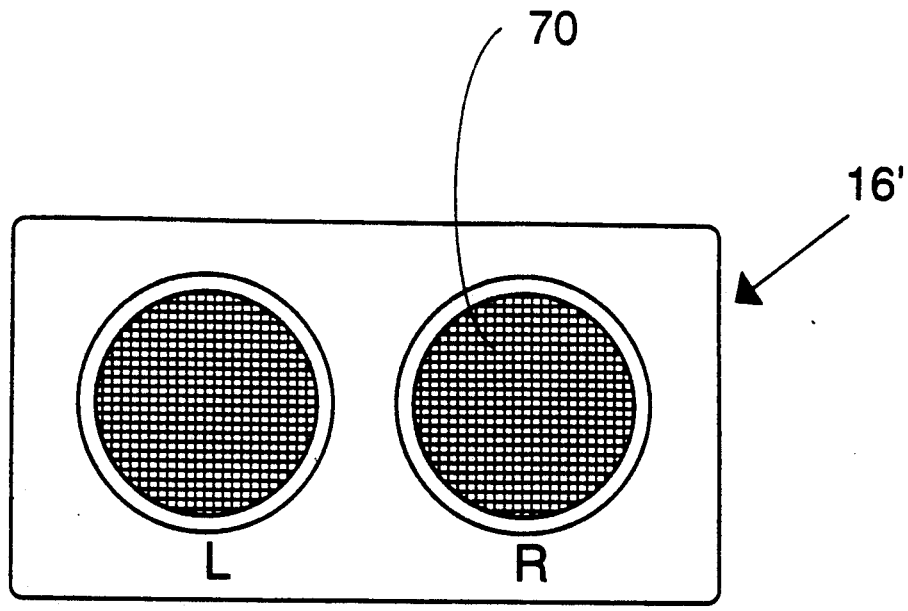
FIG. 5 is a top plan view of an alternate embodiment of lens holder apparatus for providing a shielded interior portion of a vessel for receiving contact lenses to be disinfected.

The invention is not restricted to the particular components described above. For example, lens holder apparatus may be used in which the shielded lens-receiving compartments are formed of different shielding material than that from which the compartments 32 of lens holder apparatus 16 are formed. For example, referring to FIG. 5, lens-receiving compartments of holder apparatus 16' may be defined by a double-layered knitted mesh of tin-copper-steel wire of the type available from the Tecknit Company of Cranford, New Jersey under the designation EMC Shielding Tape. The knitted wire mesh provides fluid communication between the interior of the lens-receiving compartments, yet provides effective shielding against the passage of microwave electromagnetic radiation.

In lieu of the clamp 38, a pouch may be constructed incorporating a one-way vapor vent of the type available from PyMaH Corporation of Somerville, N.J. In such case, the mouth of the pouch can be heat sealed or self-sealed using suitable adhesive. Other disinfecting solutions than saline solution may be utilized. For example, a 3% solution of hydrogen peroxide or an isotonic solution containing boric acid may be utilized. In principle, the process and apparatus of the invention need not be limited to the use of a flexible pouch, and any suitable vessel may be utilized.

Figure 6:
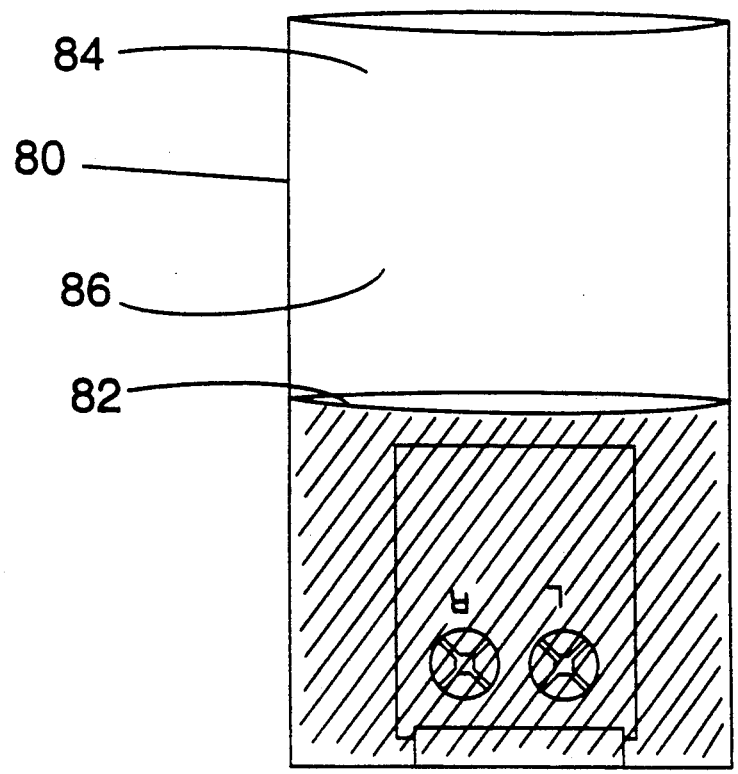
FIG. 6 is a view similar to FIG. 2 of an assembly of a pouch, lens holder apparatus and disinfecting solution, according to another embodiment of the invention.

The interior portion of the pouch which is shielded from microwave radiation may be defined by means other than the lens holder apparatus. For example, referring to FIGS. 6 and 7, a pouch 80 may be utilized formed of flexible plastic material over a surface portion of which a metallic coating 82 is deposited. Thus, the pouch 80 includes an upper part (as seen in FIG. 6) 84 which is formed of material transparent to microwave electromagnetic radiation and a lower part 86 which is formed of material that is opaque to microwave electromagnetic radiation, i.e., plastic sheet material provided with a metallic coating. The metallic coating 82 thus surrounds an interior portion of the pouch which is thereby shielded from microwave radiation.

Figure 7:
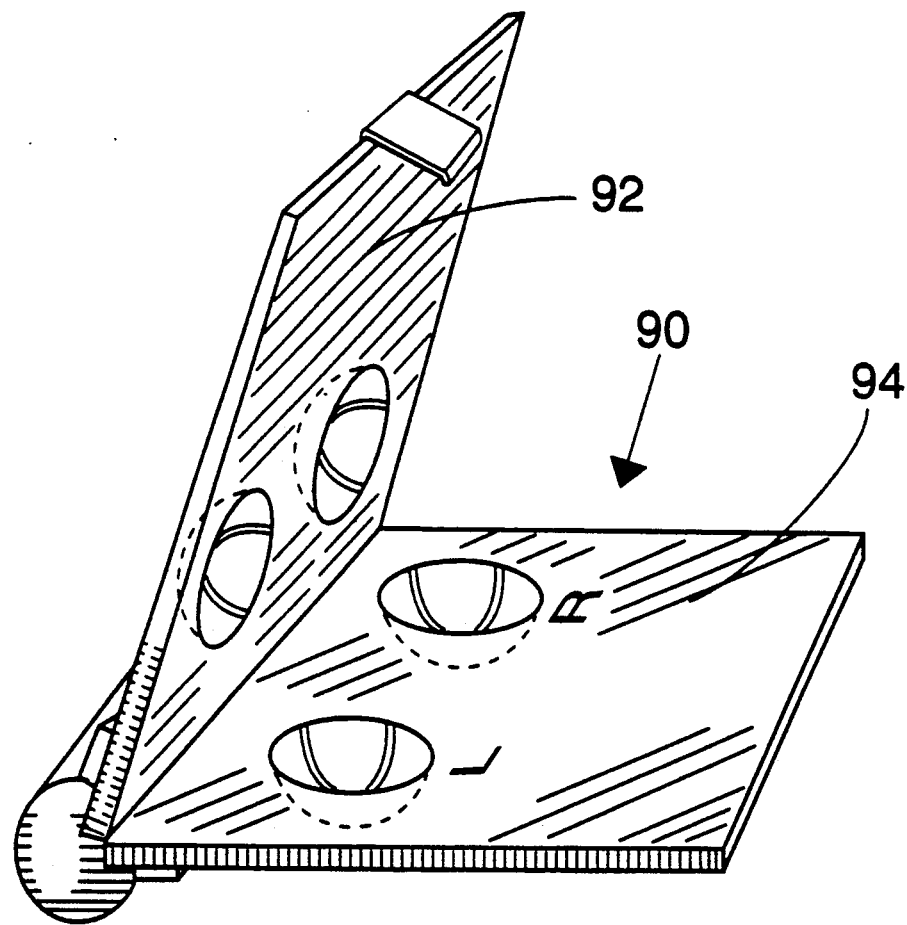
FIG. 7 is a perspective view of lens holder apparatus used in the embodiment of the invention illustrated in FIG. 6.

The contact lenses to be disinfected are situated in the shielded interior portion of pouch 80 by means of holder apparatus 90 shown in FIG. 7. Such holder apparatus is substantially conventional and is essentially defined by a pair of pivotally connected cover members 92, 94 having respective pairs of openings over which concave plastic gratings are provided to define compartments for receiving the respective contact lenses.

In use, the lenses are placed in the respective compartments of the holder apparatus 90 which is then placed in the shielded interior portion of pouch 80. Disinfecting solution is introduced into the pouch to immerse the holder apparatus and lenses. Sufficient disinfectant solution is provided so that at least a portion is situated in the unshielded interior portion of the pouch so that when the sealed assembly is exposed to microwave radiation, the disinfecting solution is heated while the lens are shielded, to thereby disinfect the lenses.

Obviously, numerous modifications and variations of the present invention are possible in the light of the above teachings. It is therefore to be understood that within the scope of the claims appended hereto, the invention may be practiced otherwise than as specifically disclosed herein.

What is claimed is:

1. A process for heat disinfecting soft contact lenses comprising the steps of:

providing a vessel at least partially formed of material transparent to microwave electromagnetic radiation;

introducing a disinfecting solution into said vessel;

placing soft contact lenses within an interior volume portion of said vessel which is substantially shielded from microwave electromagnetic radiation to prevent microwave radiation from contacting said soft contact lenses;

closing said vessel so as to be substantially liquid-tight to thereby form an assembly of said vessel, disinfecting solution and soft contact lenses; and irradiating said assembly with microwave electromagnetic radiation while said soft contact lenses are shielded from said radiation so that said soft contact lenses are not exposed to said radiation, to heat said disinfecting solution with said soft contact lenses remaining in contact with said disinfecting solution, whereby said soft contact lenses are disinfected by heat.

2. A process as recited in claim 1 wherein said soft contact lenses are maintained in contact with said disinfecting solution during said irradiating step.

3. A process as recited in claim 1 wherein said vessel comprises a collapsible pouch formed of flexible, vapor-impermeable sheet material transparent to microwave radiation.

4. A process as recited in claim 3 wherein said vapor impermeable sheet material of which said collapsible pouch is comprises a laminate of flexible polypropylene and polyester.

5. A process as recited in claim 1 wherein said irradiating step comprises irradiating said assembly to heat said disinfecting solution to a temperature at which it begins to vaporize and continuing said heating step while said soft contact lenses remain in contact with said disinfecting solution.

6. A process as recited in claim 5 wherein said vessel comprises a collapsible pouch formed of flexible vapor-impermeable sheet material transparent to microwave radiation, and wherein said collapsible pouch expands to a visibly apparent distended condition during said irradiating step.

7. A process as recited in claim 5 wherein said vessel comprises a collapsible pouch, and wherein said collapsible pouch expands to a visibly apparent distended condition during said irradiating step under the pressure of vapor produced by heating the disinfecting solution so that it boils.

8. A process as recited in claim 5 including the additional step of venting disinfecting solution vapor produced during said heating step from within said vessel.

9. A process as recited in claim 1 wherein said irradiating step comprises irradiating said assembly with microwave electromagnetic radiation at a power in the range of between about 500 to 1,000 watts.

10. A process as recited in claim 9 wherein said irradiating step comprises irradiating said assembly with microwave electromagnetic radiation at a power of about 700 watts.

11. A process as recited in claim 1 wherein said irradiating step comprises irradiating said assembly with microwave electromagnetic radiation for a time in the range of between about 15 to 60 seconds.

12. A process as recited in claim 11 wherein said irradiating step comprises irradiating said assembly with microwave electromagnetic radiation for a time of about 30 seconds.

13. A process as recited in claim 1 wherein said step of introducing disinfecting solution into said vessel comprises introducing a quantity of disinfecting solution in a range of between about 10 to 40 cubic centimeters.

14. A process as recited in claim 13 wherein said step of introducing disinfecting solution into said vessel comprises introducing a quantity of disinfecting solution of about 20 cubic centimeters.

15. A process as recited in claim 1 wherein,
said step of introducing disinfecting solution into said vessel comprises introducing a quantity of disinfecting solution in a range of between about 10 to 40 cubic centimeters, and wherein
said irradiating step comprises irradiating said assembly with microwave electromagnetic radiation at a power in the range of between 500 to 1,000 watts for a time in the range of between about 15 to 60 seconds.

16. A process as recited in claim 1 wherein said irradiating step is continued to thereby disinfect said disinfecting solution together with said soft contact lenses, and including the further step of sealing said vessel after completion of said irradiating step, and maintaining said soft contact lenses in said disinfecting solution in a disinfected condition protected from recontamination until use.

17. A process as recited in claim 1 wherein said disinfecting solution comprises saline solution.

18. A process as recited in claim 1 wherein said disinfecting solution comprises hydrogen peroxide.

19. A process as recited in claim 1 wherein prior to placing said soft contact lenses in contact with said disinfecting solution, situating said soft contact lenses in holder apparatus, said holder apparatus comprising shielding means for defining said microwave electromagnetic radiation shielded interior volume of portion of said vessel which is receivable of said soft contact lenses and in fluid communication with the surrounding interior of said vessel to permit said lenses to be in contact with said disinfecting solution.

20. A process as recited in claim 19 wherein said shielding means comprises perforated metallic sheet material.

* * * * *